(12) United States Patent
Sawa (10) Patent No.: US 9,291,538 B2
(45) Date of Patent: Mar. 22, 2016

(54) HARDNESS TESTER AND PROGRAM (71) Applicant: MITUTOYO CORPORATION, Kanagawa (JP)

(72) Inventor: Takeshi Sawa, Kawasaki (JP)

(73) Assignee: MITUTOYO CORPORATION, Kanagawa (JP)

(*) Notice: Subject to any disclaimer, the term of this patent is extended or adjusted under 35 U.S.C. 154(b) by 357 days.

(21) Appl. No.: 13/705,536

(22) Filed: Dec. 5, 2012

(65) Prior Publication Data

US 2013/0174653 A1 Jul. 11, 2013

(30) Foreign Application Priority Data

Jan. 6, 2012 (JP) ................................ 2012-001009

(51) Int. Cl.
*G01N 3/42* (2006.01)
(52) U.S. Cl.
CPC .......... *G01N 3/42* (2013.01); *G01N 2203/0082* (2013.01); *G01N 2203/0218* (2013.01)
(58) Field of Classification Search
CPC ............ G01N 3/42; G01N 2203/0082; G01N 2203/0208; G01N 3/068; G01N 3/48; G01N 2203/0218
USPC ................................................. 73/78, 81, 82
See application file for complete search history.

(56) References Cited

U.S. PATENT DOCUMENTS

| 6,142,010 A * | 11/2000 | Merck et al. ..................... 73/81 |
| 2009/0044609 A1* | 2/2009 | Sawa et al. ........................ 73/81 |
| 2010/0313638 A1* | 12/2010 | Handschuck et al. ............ 73/81 |
| 2012/0101743 A1* | 4/2012 | Sawa et al. ..................... 702/41 |

FOREIGN PATENT DOCUMENTS

| JP | 9-79963 | 3/1997 |
| JP | 3731047 | 1/2006 |
| JP | 3839512 | 11/2006 |

OTHER PUBLICATIONS

Official Action, with English-language translation thereof, for JP App. No. 2012-001009 having a mailing date of Nov. 4, 2015.

* cited by examiner

*Primary Examiner* — Hezron E Williams
*Assistant Examiner* — David Z Huang
(74) *Attorney, Agent, or Firm* — Greenblum & Bernstein, P.L.C.

(57) ABSTRACT

The present invention provides a hardness tester capable of accurately detecting a point where an indenter contacts a sample in instrumented indentation testing. Prior to beginning measurement, the hardness tester defines an expected range for a value for a displacement, speed, or acceleration of an indenter during a process of approaching a sample. After measurement has begun, the hardness tester measures the value for the displacement, speed, or acceleration of the indenter during the process of approaching the sample. When the measured value is not within the expected range, the hardness tester determines that detection of a zero point has failed.

9 Claims, 8 Drawing Sheets

HARDNESS TESTER AND PROGRAM

CROSS-REFERENCE TO RELATED APPLICATIONS

The present application claims priority under 35 U.S.C. §119 of Japanese Application No. 2012-001009, filed on Jan. 6, 2012, the disclosure of which is expressly incorporated by reference herein in its entirety.

BACKGROUND OF THE INVENTION

1. Field of the Invention

The present invention relates to a hardness tester and a program.

2. Description of Related Art

Conventionally, a testing method is known called instrumented indentation testing (nanoindentation) in which a test force (force with which a load is placed on an indenter) and a pressing depth (amount of displacement of the indenter) are continuously measured during a process where a predetermined load is placed on the indenter to press the indenter into a surface of a sample and form an indentation. A pressing curve obtained from the measurements is then analyzed to find mechanical characteristics of a material.

In general, in instrumented indentation testing, a uniform test force is applied to the indenter, which approaches the sample at a uniform speed. A point is then detected where the displacement amount changes or the speed of the indenter changes when the indenter makes contact with the sample. The test is begun with that point serving as a surface of the sample (zero point). Therefore, accuracy in detection of the point where the indenter contacts the sample (zero point) influences precision of test results for the instrumented indentation testing. Thus, a variety of innovations have been conventionally employed as a method for detecting the zero point. For example, Japanese Patent Publication No. 3731047 discloses a technique for detecting a point where an indenter contacts a sample by sending micro-vibrations through the indenter, then approaching the indenter toward the sample and detecting a change in the vibrations. Alternatively, Japanese Patent Publication No. 3839512 discloses a technique for determining the zero point by obtaining load data and displacement data before the indenter touches the sample, then detecting changes in the approach of the indenter either after contact or after testing.

SUMMARY OF THE INVENTION

However, in the methods of Japanese Patent Publication Nos. 3731047 and 3839512, when the indenter is displaced due to effects from disturbances such as vibration, this displacement may be misread as the zero point and a large error may arise in the detection of the zero point. In addition, a user of the tester (data analyzer) requires a certain amount of experience in order to assess data in which the zero point detection has failed. Therefore, the user of the tester may be unable to determine whether the zero point has been appropriately detected.

The present invention provides a hardness tester and a program capable of accurately detecting of a point where the indenter contacts the sample during an instrumented indentation test.

In order to address the above circumstances, a first aspect of the invention is a hardness tester that includes an indentation formation mechanism and a measurer. The indentation formation mechanism provides a predetermined load to an indenter and presses the indenter into a surface of a sample to form an indentation. The measurer detects a pressing depth of the indenter and a test force loaded on the indenter at the time of indentation formation to measure a pressing curve. The hardness tester further includes a definer and a determiner. Prior to beginning a measurement, the definer defines an expected range of a value for one of a displacement, speed, and acceleration of the indenter during a process of approaching the sample. After beginning the measurement, the determiner measures the value for one of the displacement, speed, and acceleration of the indenter during the process of approaching the sample and, when a measured value is not within the expected range, determines that detection of a zero point has failed.

A second aspect of the invention is the hardness tester described in the first aspect including a display displaying the expected range along with the measured value for one of the displacement, speed, and acceleration of the indenter during the process of approaching the sample.

A third aspect of the invention is the hardness tester described in one of the first and second aspects including a memory and a notifier. The memory stores pattern data and improvement information. When measurements are performed in a plurality of different testing environments outside a predefined standard testing environment, the pattern data for the value for one of the displacement, speed, and acceleration of the indenter during the process of approaching the sample is obtained for each testing environment. The improvement information relates to an improvement method for improving the testing environment in which the pattern data is obtained. When the determiner has determined that detection of the zero point has failed, the notifier compares the measured value to the pattern data stored in the memory in order to infer the testing environment, then notifies the user of the improvement information relating to the improvement method for the testing environment.

A fourth aspect of the invention is the hardness tester according to any of the first to third aspects including a stopper stopping measurement when the determiner has determined that detection of the zero point has failed.

A fifth aspect of the invention is a program enabling a computer to act as a measurer, a definer, and a determiner. The measurer provides a predetermined load to an indenter and presses the indenter into a surface of a sample to form an indentation, then detects a pressing depth of the indenter and a test force loaded on the indenter at the time of indentation formation to measure a pressing curve. Prior to beginning a measurement, the definer defines an expected range of a value for one of a displacement, speed, and acceleration of the indenter during a process of approaching the sample. After beginning the measurement, the determiner measures the value for one of the displacement, speed, and acceleration of the indenter during the process of approaching the sample and, when a measured value is not within the expected range, determines that detection of a zero point has failed.

The present invention includes the definer, which defines the expected range of the value for one of the displacement, speed, and acceleration of the indenter during the process of approaching the sample prior to beginning the measurement, and the determiner, which measures the value for one of the displacement, speed, and acceleration of the indenter during the process of approaching the sample after beginning the measurement and, when the measured value is not within the expected range, determines that detection of the zero point has failed. Thus, by defining the expected range in advance, even when the indenter deviates from the expected range due to the influence of disturbances, this deviation can automatically be determined to be a failure in the detection of the zero point. Accordingly, failure data in which detection of the zero point failed can be quantitatively excluded. Thus, even when the user lacks experience, the user will not visually mistake whether the zero point has been appropriately detected. Thus, detection of the point where the indenter contacts the sample (the zero point) can be performed accurately and with stability.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

Hereafter, a hardness tester according to the present invention is described in detail with reference to the drawings.

A hardness tester 100 according to the present embodiment is an instrumented indentation tester capable of continuously monitoring a load placed on an indenter 3 (test force) and a displacement of the indenter 3 (pressing depth).

Figure 1:
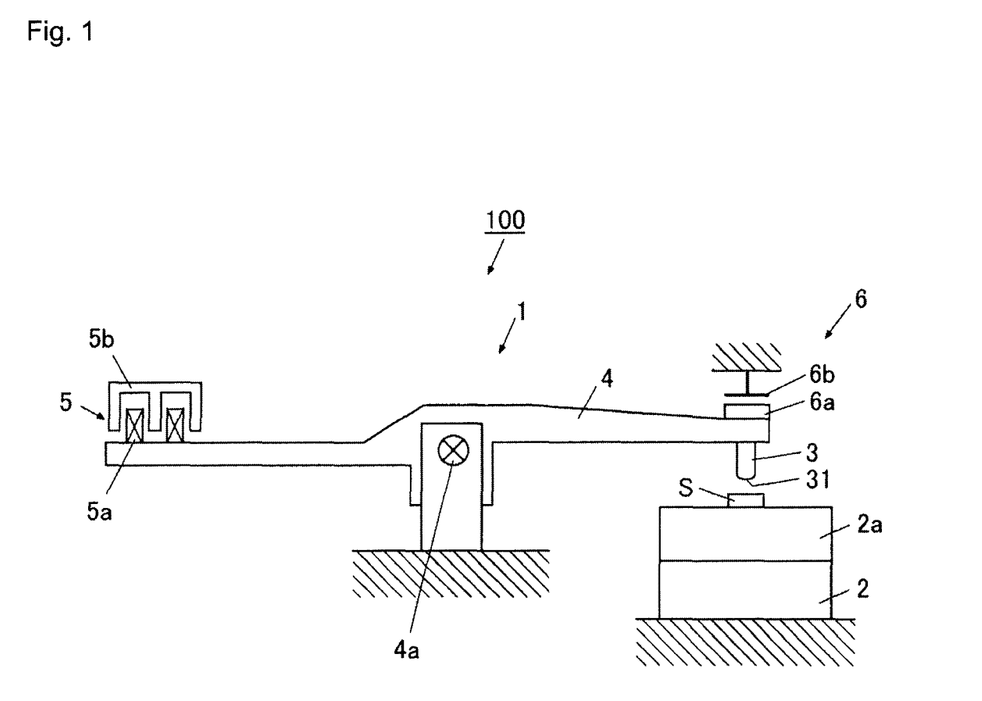
FIG. 1 is a schematic view of a hardness tester according to an embodiment of the present invention.
Figure 2:
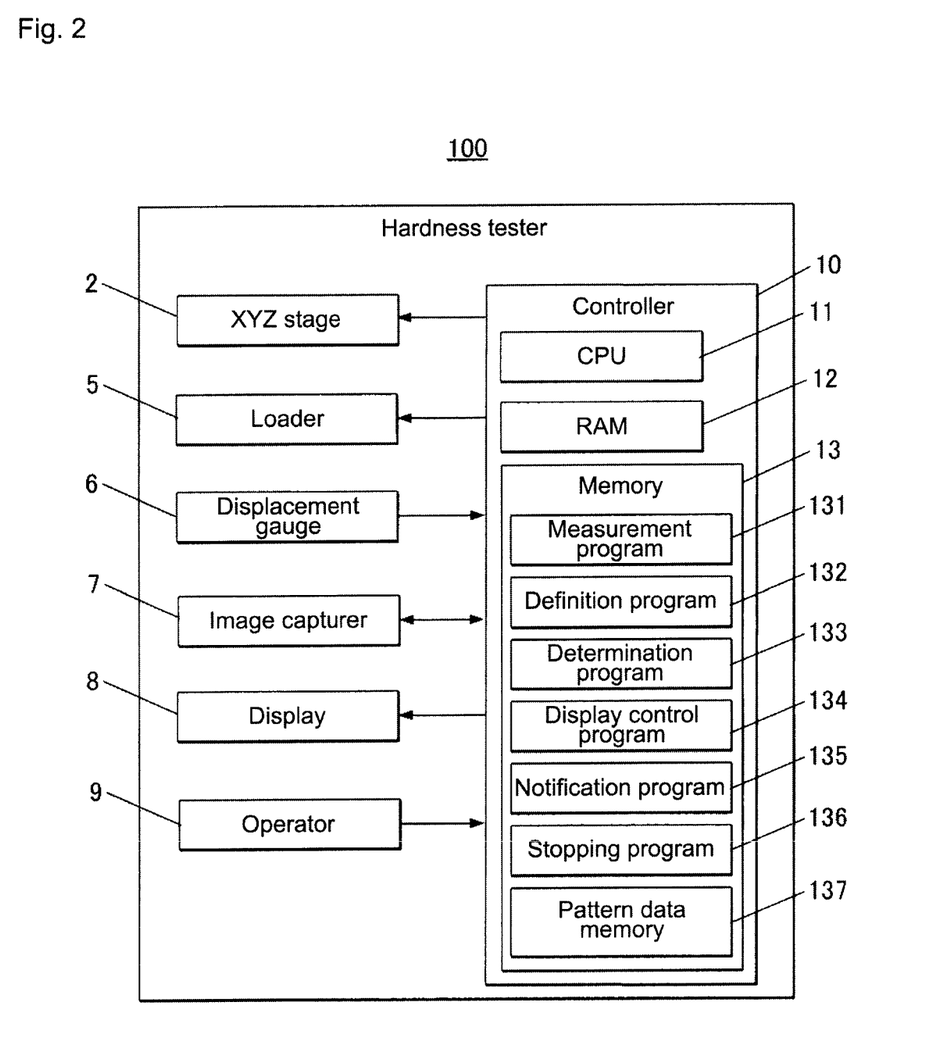
FIG. 2 is a block diagram of a control structure for the hardness tester of FIG. 1.

As shown in FIGS. 1 and 2, for example, the hardness tester 100 includes a hardness tester main body 1 to which each component is provided and a controller 10 performing all-inclusive control of the hardness tester main body 1.

The hardness tester main body 1 includes, as an indentation formation mechanism, an XYZ stage (sample stage) 2 displacing a sample S in X, Y, and Z directions; a load lever 4 having at one end thereof an indenter 3, which forms the indentation in the sample S; a loader 5 placing a predetermined load (test force) on the load lever 4; a displacement gauge 6 detecting an amount of displacement for the indenter 3; an image capturer 7 capturing an image of the indentation formed on a surface of the sample S; a display 8; and an operator 9.

The XYZ stage 2 is configured to displace in X, Y, and Z directions (i.e., in horizontal and vertical directions) according to a control signal input from the controller 10. The sample S is displaced forward/backward, to the left/right, and upward/downward by the XYZ stage 2 so as to adjust a position of the sample S with respect to the indenter 3. In addition, the XYZ stage 2 holds the sample S with a sample holding stage 2a such that the sample S resting on an upper surface thereof does not shift during test measurement. Moreover, a surface of the XYZ stage 2 and a test surface of the sample S are not necessarily required to be parallel.

Examples of the sample S include DLC, silicon rubber, and natural rubber. Specifically, the hardness tester 100 of the present embodiment is able to measure thin films such as vapor-deposited film and semiconductor materials; surface treatment layers; various kinds of plastics; various kinds of rubber; fragile materials such as micro-filaments, glass, and ceramics; and microelectronics.

The indenter 3 is provided so as to be vertically displaceable above the XYZ stage 2, on which the sample S is placed. The predetermined load is placed on the indenter 3, a bottom end (tip) 31 of which is pressed vertically into an upper surface (test surface) of the sample S, thus forming the indentation in the upper surface of the sample S. Specifically, a Vickers quadrangular pyramid indenter (angle between opposite faces is 136±0.5°), a Bercovic triangular pyramid indenter (angle formed by indenter axis and a surface is 65.03° or 65.27°), a round pyramid indenter (apex angle is 120±0.35°, or the like), and a Knoop rhomboid pyramid (opposing rhombic angles are 172° 30' and 130°) can be used as the indenter 3.

The load lever 4 is, for example, formed to be substantially pole-shaped. The load lever 4 is fixed at an approximately central portion thereof atop a stand via a cross spring 4a. At a first end of the load lever 4, the indenter 3 is provided so as to freely contact and separate from the sample S from above, the sample S resting atop the sample holding stage 2a, in order to press against the surface of the sample S to form the indentation therein. At a second end of the load lever 4, a force coil 5a is provided, configuring the loader 5.

The loader 5 is, for example, a force motor and includes the force coil 5a attached to the load lever 4 and a fixed magnet 5b fixed so as to oppose the force coil 5a. According to a control signal input from the controller 10, the loader 5 employs a driving force to rotate the load lever 4, for example. The driving force is a force generated by electromagnetic induction between a magnetic field created in a gap by the fixed magnet 5b and an electric current flowing in the force coil 5a, which is positioned inside the gap. By rotating the load lever 4, the end of the load lever 4 on the indenter 3 side is displaced downward and the indenter 3 is pressed into the sample S.

The displacement gauge 6 is, for example, an electrostatic capacitance-type displacement sensor and includes a movable polar plate 6a provided to an end of the load lever 4 on the indenter 3 side and a fixed polar plate 6b fixed in place so as to oppose the movable polar plate 6a. For example, the displacement gauge 6 detects a variation in electrostatic capacitance between the movable polar plate 6a and the fixed polar plate 6b, and thus detects an amount of displacement when the indenter 3 forms the indentation in the sample S (pressing depth when the indenter 3 is pressed into the sample S). A displacement signal based on the detected amount of displacement is then output to the controller 10. Moreover, the electrostatic capacitance-type displacement sensor is offered as an exemplary displacement gauge 6; however, the displacement gauge 6 is not limited to this and may, for example, be an optical-type displacement sensor and an eddy current-type displacement sensor.

The image capturer 7 includes, for example, a camera and captures an image of the indentation formed on the surface of the sample S by the indenter 3 atop the sample holding stage 2a, for example, according to a control signal input from the controller 10.

Figure 3:
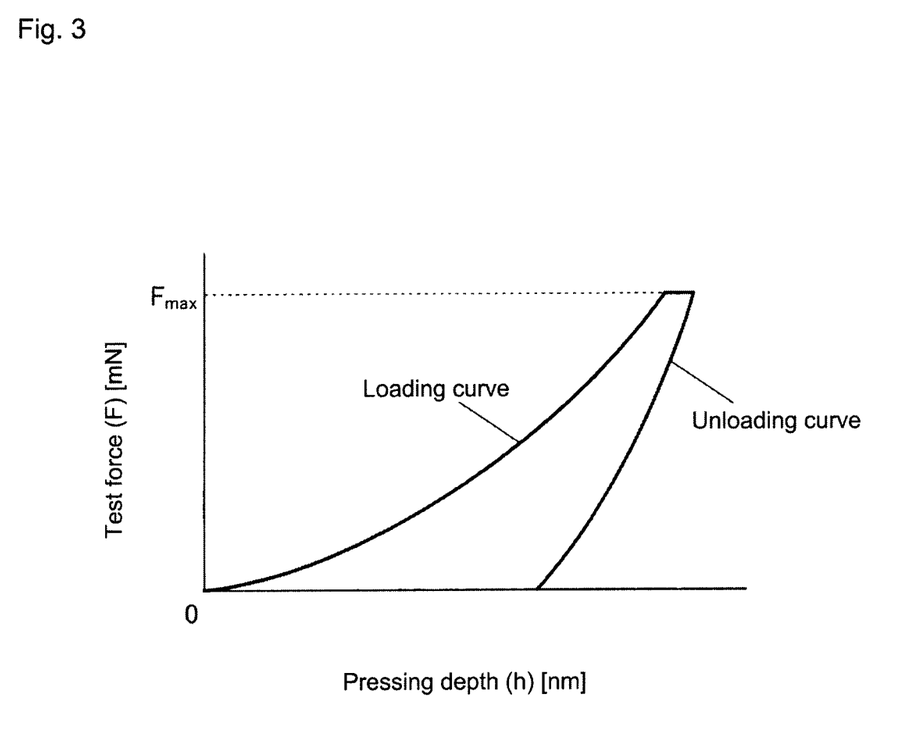
FIG. 3 is a schematic view of a pressing curve.

The display 8 is, for example, a liquid crystal display panel and performs display processing of the image of the surface of the sample S captured by the image capturer 7, various kinds of test results, and the like according to a control signal input from the controller 10. Specifically, for example, the pressing curve (see FIG. 3) measured in the process of pressing the indenter 3 into the sample S to form the indentation in the sample S; a graph (see FIGS. 4-8) illustrating a relationship between time and the displacement or speed of the indenter 3 measured in the process of the indenter 3 approaching the sample S prior to the indenter 3 contacting the sample S (hereafter referred to as an approach process); and the like are displayed on the display 8.

The operator 9 is, for example, a group of operation keys such as in a keyboard and, when operated by the user, outputs an operation signal associated with that operation to the controller 10. Moreover, the operator 9 may also include a pointing device such as a mouse or a touch screen, a remote control, and other operation devices. The operator 9 may be operated when the user performs an instruction input to perform a hardness test on the sample (measurement beginning instruction), when the user performs an instruction input to define an expected range for the displacement or speed of the indenter 3 during the approach process of the indenter 3 toward the sample S (expected range defining instruction), as well as in a case where the user defines the test force (i.e., the load) placed on the indenter 3.

The controller 10 includes a CPU (Central Processing Unit) 11, a RAM (Random Access Memory) 12, and memory 13. Through a system bus or the like, the controller 10 is connected to the XYZ stage 2, the loader 5, the displacement gauge 6, the image capturer 7, the display 8, and the operator 9.

The CPU 11 performs various control processes according to various processing programs for use in the hardness tester that are stored in the memory 13, for example.

The RAM 12, for example, includes a program storage region for extracting the processing programs executed by the CPU 11 and a data storage region storing processing results generated by input data or when the processing programs are executed.

The memory 13, for example, stores a system program executable by the hardness tester 100; various kinds of processing programs executable by the system program; data to be used when the various kinds of processing programs are executed; and data for results of the various processes calculated by the CPU 11. Moreover, programs are stored in the memory 13 in a program coding form that is readable by the computer.

Specifically, for example, a measuring program 131, a definition program 132, a determination program 133, a display control program 134, a notification program 135, a stopping program 136, and a pattern data memory 137 are stored in the memory 13.

The measuring program 131, for example, is a program that causes the CPU 11 to measure the pressing curve, in which the displacement of the indenter 3 (pressing depth (h)) and the test force loaded on the indenter 3 (F) are detected during formation of the indentation where the indenter 3 receives the predetermined load and is pressed into the surface of the sample S. When the user performs the measurement beginning instruction with the operator 9, the CPU 11 responds by executing the measuring program 131, then performs measurement of the pressing curve shown in FIG. 3 by executing the instrumented indentation test (hardness test) on the sample S.

Specific processes of the CPU 11 performed when measuring the pressing curve are described below. First, after the sample S is placed atop the sample holding stage 2a, an operation signal is input from the operator 9 instructing that a measurement be performed. The CPU 11 then performs detection of the sample surface (zero point) by applying a constant, predefined test force to the indenter 3 such that the indenter 3 approaches the sample S at a constant speed, then detecting a change in an amount of downward displacement or descent speed in the indenter 3 when the indenter 3 contacts the sample S. Specifically, a point at which the amount of downward displacement or the descent speed of the indenter 3 changes (becomes less) by contacting the sample S is detected as the zero point. When the zero point is detected, the CPU 11 switches the test force applied to the indenter 3 to the predetermined test force and thus begins the test while the predetermined test force is applied to the sample S. Next, the CPU 11 continuously measures the pressing depth (h) [nm] of the indenter 3 into the sample S during formation of the indentation and the test force (F) [mN] during formation of the indentation to obtain the pressing curve shown in FIG. 3.

More specifically, when the sample S is placed on the sample holder 2a, after input of the operation signal, the CPU 11 outputs the control signal to the loader 5. Using the force generated by the electromagnetic induction of the magnetic field created in the gap by the fixed magnet 5b of the loader 5 and the electric current flowing through the force coil 5a positioned inside the gap as the driving force to rotate the load lever 4, the CPU 11 displaces an end on the indenter 3 side of the load lever 4 downward at a constant speed such that the indenter 3 approaches the sample S. The CPU 11 thus detects the surface of the sample (zero point). The CPU 11 then outputs the control signal to the loader 5 and switches to a larger driving force so as to press the indenter 3 into the surface of the sample S and begin formation of the indentation. During formation of the indentation, the CPU 11 gradually increases the load placed on the indenter 3 until the greatest defined test force is reached. A loading curve is obtained in this process. In addition, when the CPU 11 determines that the load placed on the indenter 3 has reached the greatest test force, the CPU 11 controls the amount of electric current supplied to the driving coil to activate the loader 5, then gradually reduces the load placed on the indenter 3. An unloading curve is obtained in this process.

The CPU 11 acts as a measurer by executing the measuring program 131 of this kind.

During measurement of the pressing curve, as described above, accuracy in detection of the zero point (sample surface; the point where the indenter 3 contacts the sample S) influences precision of the test results. Thus, in order to detect the zero point with a high level of accuracy the hardness tester 100 of the present embodiment includes the definition program 132, the determination program 133, the display control program 134, the notification program 135, the stopping program 136, and the pattern data memory 137.

The definition program 132 is, for example, a program that causes the CPU 11 to define, prior to beginning measurement, the expected range of a value for the displacement (indenter descent displacement (h)) or the speed (indenter descent speed (v)) of the indenter 3 during the approach process toward the sample S. Specifically, prior to beginning measurement in the hardness test for the sample S, when the user performs the expected range definition instruction with the operator 9, the CPU 11 responds by executing the definition program 132 and defines the expected range of the value for the displacement or speed of the indenter 3 in the approach process toward the sample S.

Figure 4A:
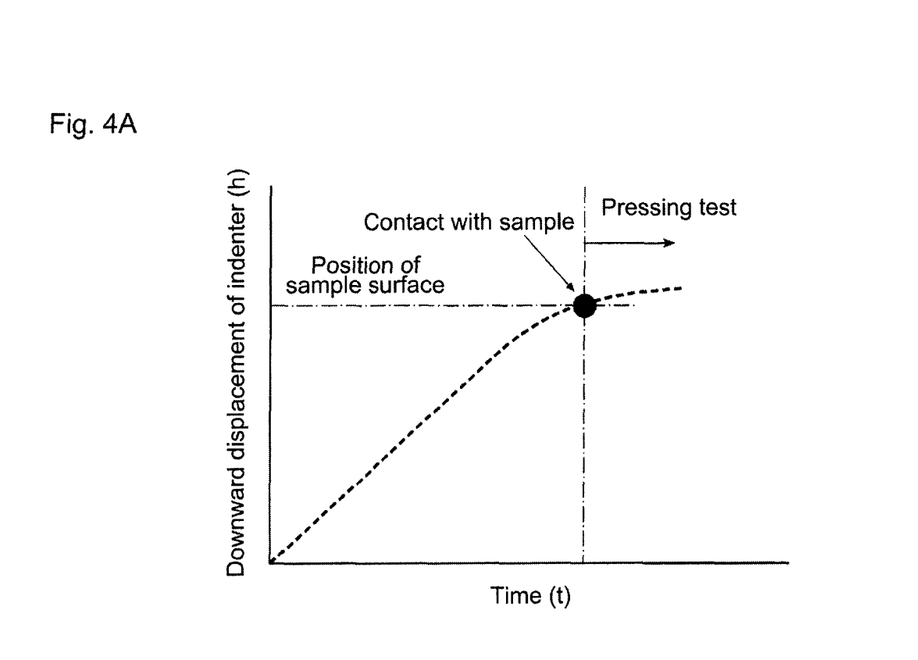
FIG. 4A is a graph showing a relationship between time and a displacement of an indenter during a process of approaching a sample.
Figure 4B:
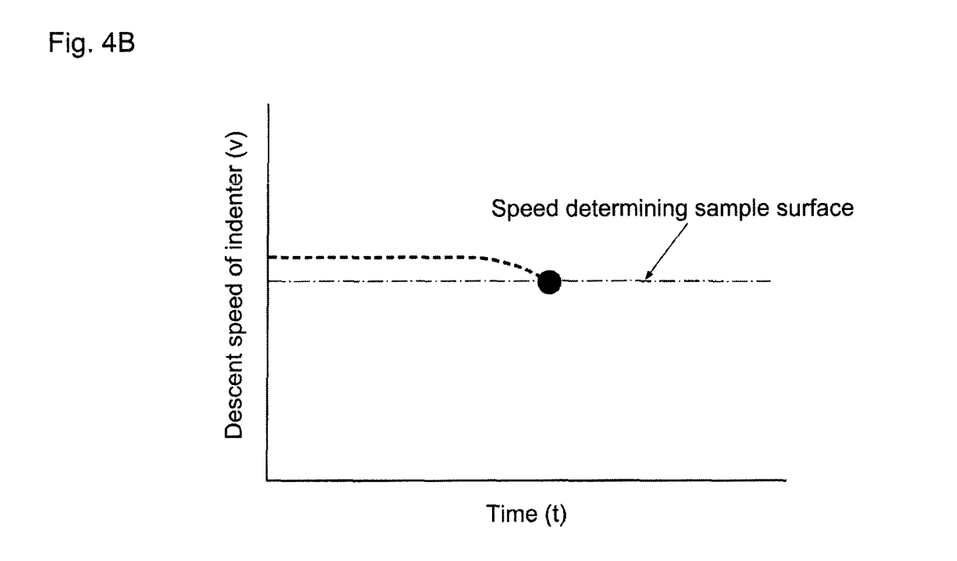
FIG. 4B is a graph showing a relationship between time and a speed of the indenter during the process of approaching the sample.

Herein, during the definition of the expected range, the position of the sample's surface is defined as a design value ahead of time, corresponding to the type of indenter 3 and sample S and to the measurement conditions. In addition, the downward displacement (h) and descent speed (v) of the indenter 3 with respect to time (t) during the approach process toward the sample S are also defined in advance as design values. Moreover, FIG. 4A is a graph illustrating the design value for the downward displacement (h) of the indenter 3 with respect to time (t). FIG. 4B is a graph illustrating the design value for the descent speed (v) of the indenter 3 with respect to time (t).

Figure 5A:
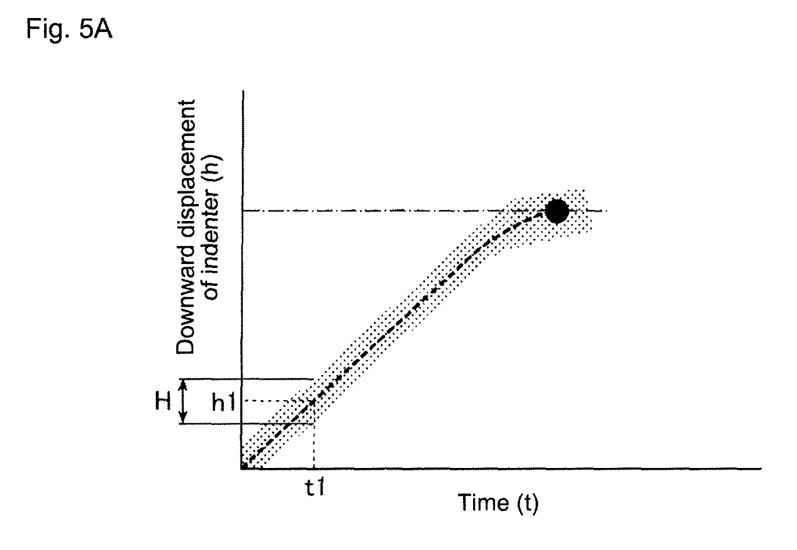
FIG. 5A is a graph showing a state where an expected range is displayed on the graph of FIG. 4A.
Figure 5B:
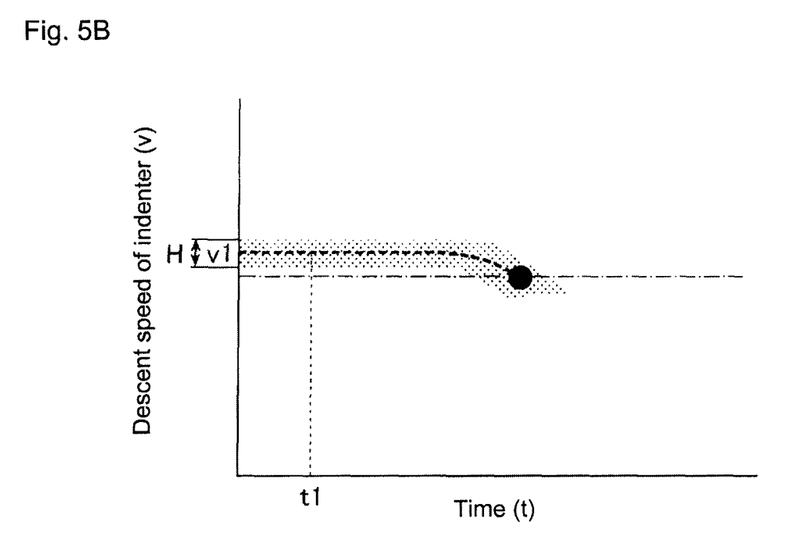
FIG. 5B is a graph showing a state where the expected range is displayed on the graph of FIG. 4B.

In a case where the expected range is defined for the value for the displacement of the indenter 3, as shown in FIG. 5A, the CPU 11 executes a predefined calculation process with respect to the design value (h=h1) for the displacement of the indenter 3 at a given time (t=t1) in the approach process, then defines a range that includes the design value within several percent as an expected range H. The range of the expected range H can also be modified as desired by the user. Similarly, when the expected range is defined for the value for the speed of the indenter 3, as shown in FIG. 5B, the CPU 11 executes the predefined calculation process with respect to the design value (v=v1) for the speed of the indenter 3 at a given time (t=t1) in the approach process, then defines a range that includes that value within several percent as the expected range H.

The CPU 11 acts as a definer by executing the definition program 132 of this kind.

Figure 6A:
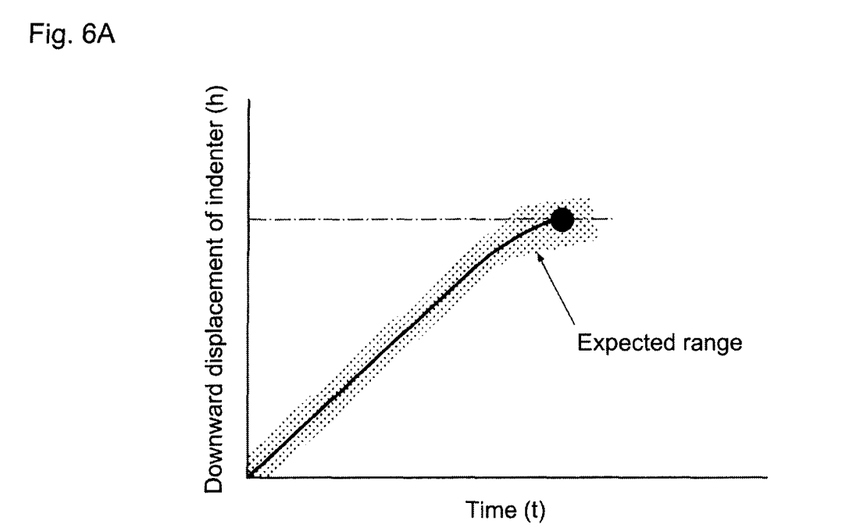
FIGS. 6A and 6B are graphs showing a state where a measured value is within the expected range.
Figure 6B:
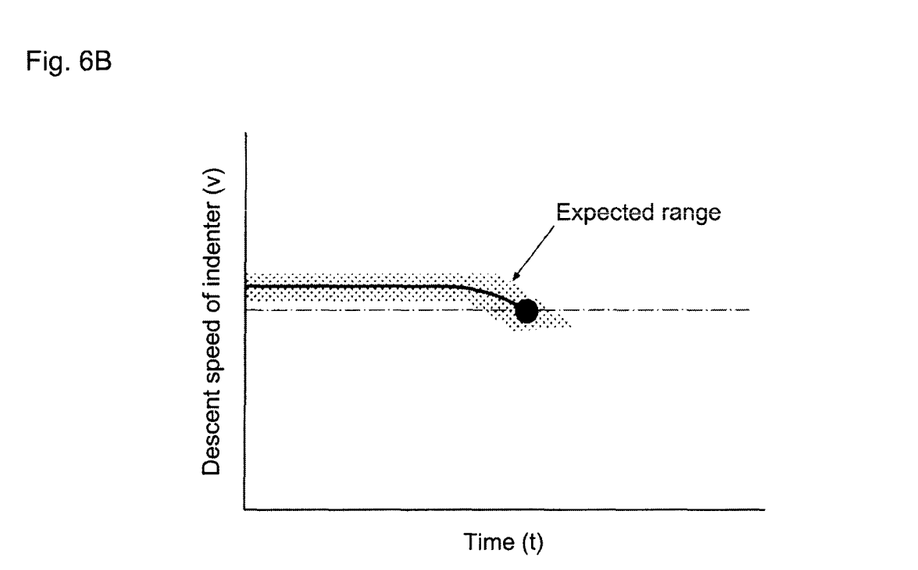
Figure 7A:
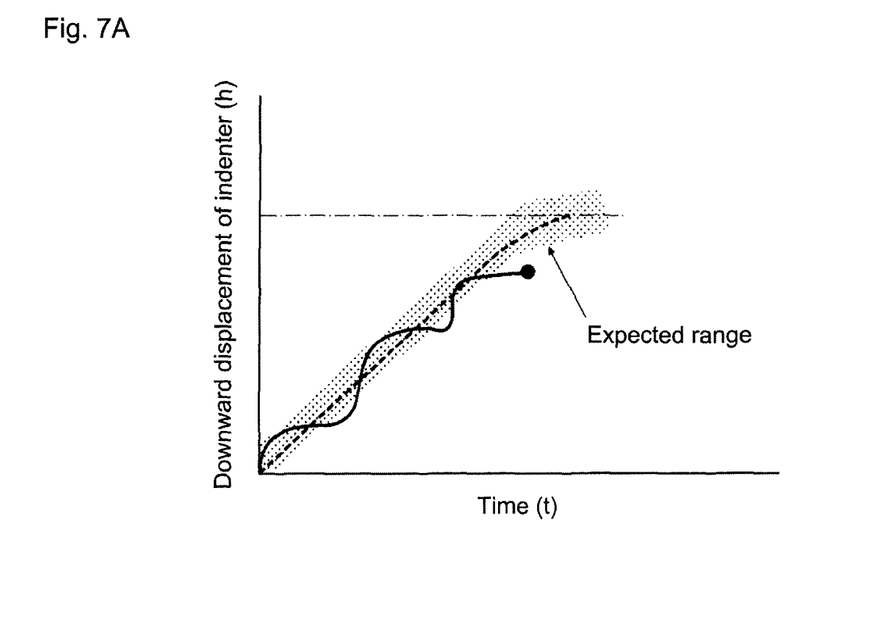
FIGS. 7A and 7B are graphs showing a state where the measured value is outside the expected range.
Figure 7B:
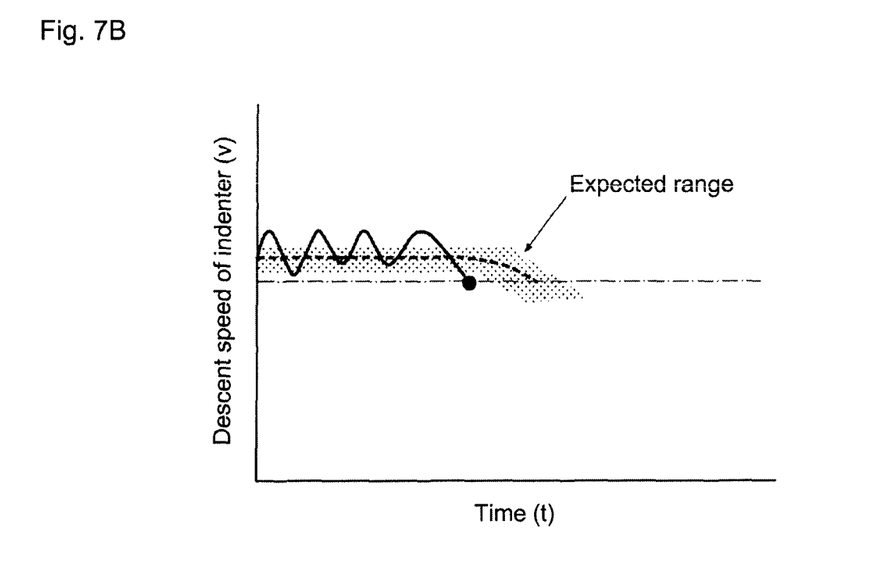
Figure 8A:
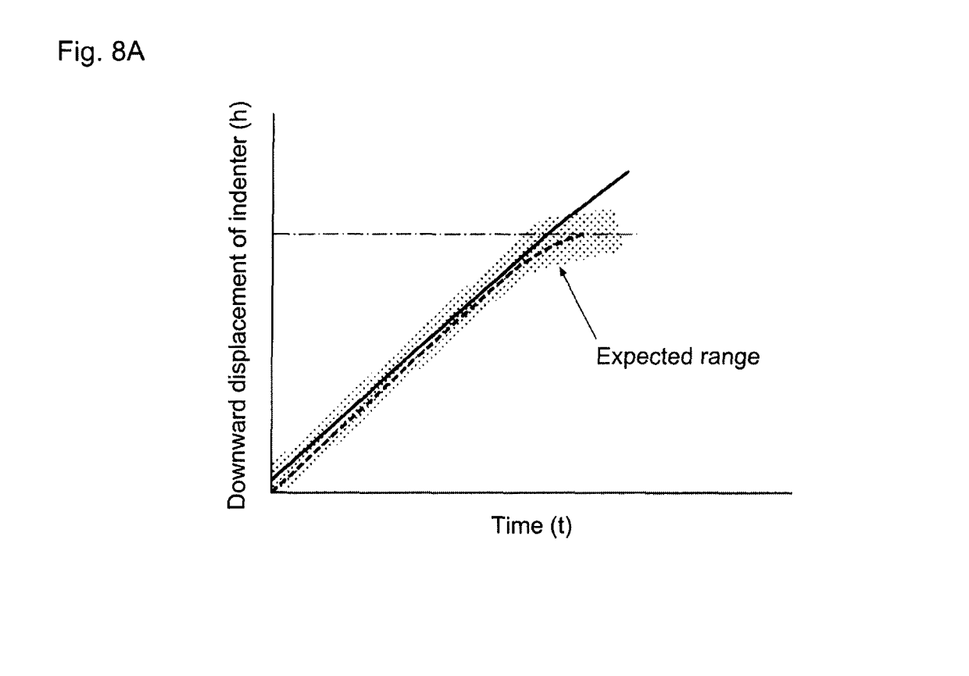
FIGS. 8A and 8B are graphs showing a state where the measured value is outside the expected range.
Figure 8B:
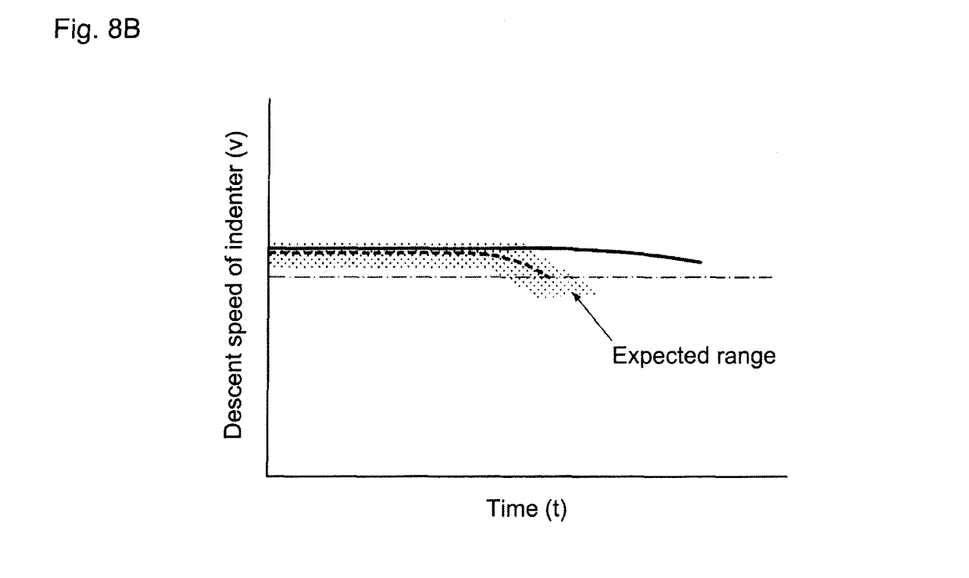

The determination program 133 is, for example, a program that causes the CPU 11 to measure, after measurement has begun, the value for the displacement or speed of the indenter 3 during the approach process toward the sample S and, when the measured value is outside the expected range, to determine that detection of the zero point has failed. Specifically, the CPU 11 measures the value for the displacement or speed of the indenter 3 during the approach process toward the sample S and, as shown in FIGS. 6A and 6B, when the measured value (solid lines in FIGS. 6A and 6B) is within the expected range, determines that the zero point has been appropriately detected. Meanwhile, as shown in FIGS. 7A-8B, when the measured value is outside the expected range, the CPU 11 determines that the zero point could not be appropriately detected. Moreover, FIGS. 7A and 7B are examples illustrating a case where the indenter approaches while shaking due to an outside influence such as vibrations or wind. FIGS. 8A and 8B are examples illustrating a state where the zero point could not be detected even in a state where the indenter advances deeply into the sample due to the extreme softness of the sample. The CPU 11 acts as a determiner by executing the determination program 133 of this kind.

The display control program 134 is a program that causes the CPU 11 to display the expected range with the measured value for the displacement or speed of the indenter 3 during the approach process toward the sample S. Specifically, by executing the display control program 134, the CPU 11 displays on the display 8 the graphs of FIGS. 4-8 described above during the measurement. By displaying the graphs exemplified in FIGS. 4-8 on the display 8, the user is able to visually judge whether the indenter 3 has approached the sample S appropriately and detection of the zero point has been performed without problems. The CPU 11 acts as a display along with the display 8 by executing the display control program 134 of this kind.

The notification program 135 is, for example, a program that causes the CPU 11 to infer a test environment by comparing the measured value with the pattern data stored in the pattern data memory 137 when detection of the zero point is determined to have failed by executing the determination program 133. The notification program 135 then causes the CPU 11 to notify the user with improvement information relating to an improvement method for the test environment. Specifically, when detection of the zero point is determined to have failed by executing the determination program 133, by executing the notification program 135, the CPU 11 compares the measured value with the pattern data stored in the pattern data memory 137, then selects the pattern data that has a similar trend in variation of the values (similar waveform), and thus infers the test environment in which the measurement was performed. Next, as the improvement information relating to the improvement method for the test environment, the CPU 11 notifies the user by displaying on the display 8 a message tied to the selected pattern data and stored in the pattern data memory 137. For example, the example of FIGS. 7A and 7B can be inferred to be in a state where the indenter is approaching while shaking due to a disturbance such as vibration or wind. The CPU 11 thus displays the message on the display 8 saying, for example, "Please improve the measurement environment." The example of FIGS. 8A and 8B can be inferred to be in a state where the sample is extremely soft, and thus the CPU 11 displays the message on the display 8 saying, for example, "Please change the measurement level." The CPU 11 acts as the notifier with the display 8 by executing the notification program 135 of this kind.

The stopping program 136 is, for example, a program causing the CPU 11 to stop measurement when detection of the zero point is determined to have failed by executing the determination program 133. Specifically, when detection of the zero point is determined to have failed by executing the determination program 133, the CPU 11 stops measurement by gradually reducing the load applied to the indenter 3. The CPU 11 acts as the stopper by executing the stopping program 136 of this kind.

The pattern data serving as a reference during execution of the notification program 135 and the messages (improvement information) displayed on the display 8 are tied together and stored in the pattern data memory (memory) 137. The pattern data is the value for the displacement, speed, or acceleration of the indenter 3 during the approach process toward the sample S obtained for each of a plurality of different test environments outside the predefined standard test environment when the measurement is performed in the plurality of different test environments. Moreover, the "standard test environment" is an ideal test environment in which the test can be performed with no influence from outside disturbances. In addition, the "test environment outside the standard test environment" may be, for example, a test environment in which the influence of outside disturbances is large and an accurate test cannot be performed, or in which an accurate test cannot be performed because the measurement level is not matched to the hardness of the sample S. This kind of pattern data may be actual measured data the user obtained by performing measurements in the test environment outside the standard test environment ahead of time, or may be values obtained by simulations in the CPU 11. The messages are the improvement information relating to the improvement method for improving the test environment in which the pattern data was obtained. The messages are tied to each set of pattern data and stored in the memory, and are used to suggest the method for improving the test environment to the user.

In a case where, prior to beginning measurement, the displacement or speed of the indenter 3 with respect to time during the approach process toward the sample S is defined as the expected range and the motion of the indenter 3 during actual measurement is outside the expected range due to an unanticipated vibration or the like, the hardness tester 100 equipped with the above-described configuration automatically determines that detection of the zero point has failed. In addition, during measurement, by displaying on the display 8 a graph showing the displacement or speed of the indenter 3 with respect to time during the approach process, the user is able to visually recognize whether detection of the zero point has been performed appropriately. In addition, when detection of the zero point is determined to have failed, the improvement method for the test environment is suggested and the measurement is stopped.

As described above, according to the present embodiment, the hardness tester 100 includes the definer (the CPU 11 and the definition program 132) and the determiner (the CPU 11 and the determination program 133). The definer defines the expected range of the value for the displacement or speed of the indenter 3 during the approach process toward the sample S prior to beginning measurement. After beginning measurement, the determiner measures the value for the displacement or speed of the indenter 3 during the approach process toward the sample S and, when the measured value is outside the expected range, determines that detection of the zero point has failed. Therefore, by defining the expected range ahead of time, even when the indenter 3 is outside the expected range due to the influence of an outside disturbance, detection of the zero point may be automatically determined to have failed. Thus, the failure data in which detection of the zero point failed can be quantitatively excluded. Therefore, even when the user lacks experience, the user will not mistake whether the zero point has been appropriately detected. Accordingly, detection of the point (zero point) where the indenter 3 contacts the sample S can be performed accurately and with stability.

According to the present embodiment, the hardness tester 100 includes a display (the CPU 11, the display control program 134, and the display 8) for displaying the expected range with the measured value for the height of the indenter 3 during the approach process toward the sample S. Accordingly, the displacement or speed of the indenter 3 during the approach process is displayed with the expected range on the display 8. Therefore, the user can visually recognize whether the indenter 3 has appropriately approached/contacted the surface of the sample S.

According to the present embodiment, the hardness tester 100 includes the memory (the pattern data memory 137) and the notifier (the CPU 11 and the notification program 135). The memory stores the pattern data for the value for the displacement, speed, or acceleration of the indenter 3 during the approach process toward the sample S and also stores the improvement information. The pattern data is obtained for each case in which the measurement is performed in the plurality of different test environments outside the predefined standard test environment. The improvement information relates to the improvement method for improving the test environment for which the pattern data is obtained. When the determiner determines that detection of the zero point has failed, the notifier infers the test environment by comparing the measured value with the pattern data stored in the pattern data memory 137, then notifies the user of the improvement information (message) relating to the improvement method for the test environment. Accordingly, when detection of the zero point is determined to have failed, the hardness tester 100 can suggest an appropriate improvement strategy to the user.

According to the present embodiment, the hardness tester 100 includes the stopper (the CPU 11 and the stopping program 136) stopping the measurement when the determiner determines that detection of the zero point has failed. Therefore, when detection of the zero point is determined to have failed, indentation formation can be stopped quickly and work can be made more efficient.

In the above-described embodiment, the definer was described to exemplify a configuration defining the expected range of the value for the displacement or speed of the indenter 3. However, the definer may also be configured to define the expected range of the value for the acceleration of the indenter 3, rather than the displacement and speed thereof.

The above-described embodiment was described to exemplify a configuration including the display, notifier, and stopper, in addition to the measurer, definer, and determiner. However, of these, the display may be omitted from the configuration. In such a case, the configuration includes at least one of the notifier and the stopper. Specifically, when the display is omitted, the user is able to recognize that the indenter 3 is outside the expected range during the approach process through at least one of the notifier and the stopper.

In a case where the display is included, in addition to the measurer, definer, and determiner, both the notifier and the stopper may be omitted from the configuration, or either one of the two may be included. Specifically, when the display is included and both the notifier and the stopper are omitted, the user visually monitors the graph displayed on the display 8 and, when necessary, stops indentation formation as desired and changes the measurement environment and the measurement level as desired. When the display and the notifier are included and the stopper is omitted, the user visually monitors the graph displayed on the display 8 and, when necessary, stops indentation formation as desired and changes the measurement environment and the measurement level with reference to the message sent from the notifier. When the display and the stopper are included and the notifier is omitted, the user visually monitors the graph displayed on the display 8 and changes the measurement environment and the measurement level as desired.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A hardness tester, comprising:
an indentation former configured to provide a predetermined load to an indenter and further configured to press the indenter into a surface of a sample to provide an indentation;
a measurer configured to perform a measurement to detect a pressing depth of the indenter and a test force loaded on the indenter at the time of indentation to obtain a pressing curve;
a definer configured to define, prior to beginning the measurement, an expected range for a value for one of a displacement, speed, and acceleration of the indenter during a process of approaching the sample for the measurement, the expected range being a function of the indenter and of the sample;
a determiner configured to measure a measured value, after beginning the measurement, for the one of the displacement, speed, and acceleration of the indenter during the process of approaching the sample and, when the measured value is not within the expected range, to determine detection of a zero point to have failed;
a memory; and
a notifier configured to compare, when the determiner has determined that detection of the zero point has failed, the measured value to data stored in the memory in order to infer a testing environment, and to notify a user of information relating to improvement of the testing environment.

2. The hardness tester according to claim 1, further comprising a display configured to display the expected range with the measured value for one of the displacement, speed, and acceleration of the indenter during the process of approaching the sample.

3. The hardness tester according to claim 2, further comprising a stopper configured to stop the measurement when the determiner has determined that detection of the zero point has failed.

4. The hardness tester according to claim 1, wherein
the memory is configured to store pattern data and improvement information,
the pattern data for the value for one of the displacement, speed, and acceleration of the indenter during the process of approaching the sample is obtained for each of a plurality of different testing environments outside a predefined standard testing environment when the measurement is performed in the testing environments, and
the improvement information relates to an improvement method for improving the testing environment in which the pattern data is obtained.

5. The hardness tester according to claim 4, further comprising a stopper configured to stop the measurement when the determiner has determined that detection of the zero point has failed.

6. The hardness tester according to claim 1, further comprising a stopper configured to stop the measurement when the determiner has determined that detection of the zero point has failed.

7. A hardness tester, comprising:
an indentation former configured to provide a predetermined load to an indenter and further configured to press the indenter into a surface of a sample to provide an indentation;
a measurer configured to perform a measurement to detect a pressing depth of the indenter and a test force loaded on the indenter at the time of indentation to obtain a pressing curve;
a definer configured to define, prior to beginning the measurement, an expected range for a value for one of a displacement, speed, and acceleration of the indenter during a process of approaching the sample for the measurement, the expected rang a function of the indenter and of the sample;
a determiner configured to measure a measured value, after beginning the measurement, for the one of the displacement, speed, and acceleration of the indenter during the process of approaching the sample and, when the measured value is not within the expected range, to determine detection of a zero point to have failed;
a memory configured to store pattern data and improvement information, wherein:
the pattern data for the value for one of the displacement, speed, and acceleration of the indenter during the process of approaching the sample is obtained for each of a plurality of different testing environments outside a predefined standard testing environment when the measurement is performed in the testing environments, and
the improvement information relates to an improvement method for improving the testing environment in which the pattern data is obtained; and
a notifier configured to compare, when the determiner has determined that detection of the zero point has failed, the measured value to the pattern data stored in the memory in order to infer the testing environment, and to notify a user of the improvement information relating to the improvement method for the testing environment.

8. The hardness tester according to claim 7, further comprising a stopper configured to stop the measurement when the determiner has determined that detection of the zero point has failed.

9. At least one non-transitory computer readable medium that stores a computer program for enabling a computer to act as a measurer, a definer, a determiner, and a notifier, the computer program when executed by a processor of the computer, causing the computer to perform operations comprising:
providing a predetermined load to an indenter and pressing the indenter into a surface of a sample to provide an indentation, and then detecting a measurement of a pressing depth of the indenter and a test force loaded on the indenter at the time of indentation formation to obtain a pressing curve,
causing the definer to define, prior to beginning the measurement, an expected range for a value for one of a displacement, speed, and acceleration of the indenter during a process of approaching the sample for the measurement, the expected range being a function of the indenter and the sample,
causing the determiner to measure a measured value, after beginning the measurement, for the one of the displacement, speed, and acceleration of the indenter during the process of approaching the sample and, when the measured value is not within the expected range, to determine detection of a zero point to have failed, and
causing the notifier to compare, when the determiner has determined that detection of the zero point has failed, the measured value to data stored in a memory in order to infer a testing environment and notifying a user of information relating to improvement of the testing environment.

* * * * *